(12) United States Patent
Xue et al.

(10) Patent No.: US 9,848,797 B2
(45) Date of Patent: Dec. 26, 2017

(54) PATIENT TABLES AND MAGNETIC RESONANCE IMAGING EQUIPMENT

(71) Applicants: Ting Qiang Xue, Shenzhen (CN); Xu Yan, Shenzhen (CN)

(72) Inventors: Ting Qiang Xue, Shenzhen (CN); Xu Yan, Shenzhen (CN)

(73) Assignee: Siemens Aktiengesellschaft, München (DE)

( * ) Notice: Subject to any disclaimer, the term of this patent is extended or adjusted under 35 U.S.C. 154(b) by 793 days.

(21) Appl. No.: 14/144,194

(22) Filed: Dec. 30, 2013

(65) Prior Publication Data

US 2014/0184225 A1 Jul. 3, 2014

(30) Foreign Application Priority Data

Dec. 31, 2012 (CN) .......................... 2012 1 0591452

(51) Int. Cl.
*A61B 5/05* (2006.01)
*A61B 5/055* (2006.01)
*A61B 5/00* (2006.01)

(52) U.S. Cl.
CPC ............ *A61B 5/0555* (2013.01); *A61B 5/704* (2013.01)

(58) Field of Classification Search
CPC ...... A61B 5/0555; A61B 5/704; A61G 7/012; A61G 13/06
USPC .................................................. 5/611, 620
See application file for complete search history.

(56) References Cited

U.S. PATENT DOCUMENTS

| 4,159,822 | A | * | 7/1979 | Ota | A47C 3/30 |
| | | | | | 5/614 |
| 4,582,310 | A | * | 4/1986 | Hahn | A61G 13/06 |
| | | | | | 254/122 |
| 4,712,653 | A | * | 12/1987 | Franklin | B66F 7/08 |
| | | | | | 108/145 |
| 5,802,638 | A | * | 9/1998 | Parker | A61G 7/018 |
| | | | | | 5/600 |
| 2006/0174412 | A1 | | 8/2006 | Hornig | |
| 2008/0028526 | A1 | * | 2/2008 | Kato | A61B 5/0555 |
| | | | | | 5/601 |
| 2008/0127416 | A1 | | 6/2008 | Tigwell | |
| 2009/0252300 | A1 | * | 10/2009 | Schwartz | G01G 19/445 |
| | | | | | 378/209 |

(Continued)

FOREIGN PATENT DOCUMENTS

| CN | 2680201 Y | 2/2005 |
| CN | 1817335 | 8/2006 |

(Continued)

*Primary Examiner* — David M Gray
*Assistant Examiner* — Laura Roth
(74) *Attorney, Agent, or Firm* — Lempia Summerfield Katz LLC

(57) ABSTRACT

A patient table includes a table body configured for bearing a patient, a connecting rod structure configured for supporting the table body, and a spring structure. The connecting rod structure is operable such that the table body may perform a lifting motion between a high position and a low position. Both ends of the spring structure are fixed. At least a first end of the spring structure is hinged to the connecting rod structure. The spring structure may be used for driving the lifting motion of the connecting rod structure and/or bearing the table body. The patient table may be used for nuclear magnetic resonance imaging equipment.

14 Claims, 6 Drawing Sheets

(56) References Cited

U.S. PATENT DOCUMENTS

2010/0080344 A1    4/2010  Schilling et al.
2014/0325759 A1*  11/2014  Bly .................... A61G 7/002
                                                    5/611

FOREIGN PATENT DOCUMENTS

| CN | 1969747      |    5/2007 |
| CN | 201822988 U  |    5/2011 |
| CN | 202173545 U  |    3/2012 |
| EP | 2168484      |    3/2010 |
| JP | 2000342639 A |   12/2000 |
| WO | WO2012048378 A1 | 4/2012 |

\* cited by examiner

PATIENT TABLES AND MAGNETIC RESONANCE IMAGING EQUIPMENT

RELATED APPLICATIONS

This application claims the benefit of Chinese Patent Application No. CN 201210591452.2, filed Dec. 31, 2012, the entire contents of which are hereby incorporated herein by reference.

TECHNICAL FIELD

The present teachings relate generally to patient tables (e.g., for use in imaging equipment, such as nuclear magnetic resonance imaging equipment) and to nuclear magnetic resonance imaging (MRI) equipment having such patient tables.

BACKGROUND

For many examinations that use imaging equipment such as nuclear magnetic resonance imaging (MRI) equipment, computed tomography (CT) equipment, and other X-ray examination equipment, the patient is lying down on a patient table (PTAB). Due to limitations of physical condition of the patient, the patient may only be examined when lying down on the patient table.

At least a part of the patient table (e.g., a top board) may move horizontally. After the patient lies down on the patient table, the horizontally movable part may move from a position outside the examination equipment to a target examination position.

Several approaches have been used to facilitate patient placement on a patient table. For example, in commonly-assigned Chinese patent ZL200610005074.X, a patient table configured for use in an X-ray system and a control method are described. To facilitate safe, easy mounting of a patient onto a patient table, the patient table is provided with a patient mounting aider. The patient mounting aider includes at least one extendable and retractable and/or fold-up and fold-down foot step.

An alternative way to assist a patient in mounting onto a patient table is to provide the patient table with a capability to lift vertically. The vertically lifting capability may be provided by a vertical actuator.

For example, the vertical lifting motion of a patient table described in European patent application publication number EP 2168484 A1 is provided by a vertical lifting drive apparatus that includes a vertical lifting electric motor. The vertical drive apparatus does work bearing all of the load weight of the patient table during the lifting process.

In other patient tables, other drive apparatuses may be provided to drive the motion of the patient table. A patient platform used for equipment that is easily affected by electrical or magnetic interference (e.g., an MRI scanner) is described in the commonly-assigned Chinese patent application publication number CN 1969747 A. The patient platform is moved horizontally or vertically by a hydraulic apparatus rather than electric motors since electric motors may generate interference for the equipment.

To save costs, a patient table may be equipped with a drive apparatus configured for moving in only the horizontal direction and a set of manual vertical lifting auxiliary tools for lifting the patient table. For example, the vertical lifting auxiliary tool may include a lifting-jack-type or mechanical-lead-screw-type mechanism. The patient table may include a high-position pin hole and a low-position pin hole. An operator may jack up or lower the patient table (e.g., top board) manually by the mechanism, and insert a pin into the preceding pin hole to position the patient table at the desired high position or low position. Such a manual motion mechanism has mechanical self-locking. The efficiency of the manual motion mechanism is relatively low, and the operation is time-consuming and power-consuming.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a patient platform that uses a minimum of lifting motion operating force is provided. In some embodiments, the patient platform is widely applicable to various types of imaging equipment (e.g., MRI), and has a structure that is simple, inexpensive, and easy to operate.

In some embodiments, a patient table is provided for minimizing the operating force of the lifting motion. In some embodiments, the operating force is so small that the operating staff may manually operate the lifting motion of the patient table without using external tools.

In some embodiments, a patient table that includes a table body configured for bearing a patient, a connecting rod structure configured for supporting the table body, and a spring structure is provided. The connecting rod structure is operable to move the table body (e.g., in a lifting motion) between a high position and a low position. Both ends of the spring structure are fixed. At least a first end of the spring structure is hinged to the connecting rod structure, and the spring structure may be used for driving the lifting motion of the connecting rod structure and/or bearing the table body.

The patient table supports the patient table body and/or drives the table body during a lifting motion using the elastic force of the spring structure. As a result, power consumption of the vertical lifting actuator may be reduced or eliminated, thereby reducing costs and energy consumption. Alternatively, the operating staff may operate the patient table manually with a manual tool that is simpler than a corresponding conventional tool or in the absence of any manual tool, thereby likewise reducing costs.

In some embodiments, the table body may include a top board and a rack configured for bearing a patient. The top board is supported on the rack and configured for horizontal movement. The patient table may also include a horizontal actuator configured for driving the top board to move horizontally.

In some embodiments, the patient table is configured for use in nuclear magnetic resonance imaging equipment that includes a magnet or a superconducting magnet configured to generate a static magnetic field. In some embodiments, at least at the high position and/or the low position, an included angle between the extension orientation of the spring structure and the direction of a nearby static magnetic field thereof is less than or equal to ±15°, in some embodiments less than or equal to ±10°, and in some embodiments less than or equal to ±5°. In some embodiments, the extension orientation of the spring structure is substantially parallel to the direction of the static magnetic field. In some embodiments, within the entire lifting motion range of the patient table, an included angle between the extension orientation of the spring structure and the direction of a nearby static magnetic field is less than or equal to ±15°, in some embodiments less than or equal to ±10°, and in some embodiments less than or equal to ±5°. The extension orientation of the spring structure may be substantially parallel to the direction of the static magnetic field. In some embodiments, the inclination angle of the spring structure with respect to a nearby static magnetic field does not exceed a certain value.

In some embodiments, an included angle between an extension orientation of the spring structure and a horizontal direction is less than or equal to ±15°, in some embodiments less than or equal to ±10°, and in some embodiments less than or equal to ±5°. In some embodiments, the spring structure is horizontally oriented. A horizontal orientation may be used, for example, when the patient table is to be used in nuclear MRI equipment since the magnetic field generated by the magnet or superconducting magnet may extend horizontally at the position of the patient table (e.g., at the position of the spring structure extension arrangement).

As described in application CN 1969747 A, large medical imaging equipment (e.g., nuclear MRI equipment or MRI equipment, such as superconducting nuclear MRI equipment) is susceptible to interference from other magnetic fields, and may generate special operating environments in the surroundings.

The operation of magnetic resonance equipment is based on the interaction between a strong static magnetic field generated by a superconducting magnet or a magnet, a gradient magnetic field generated by a gradient system, and a special electromagnetic field generated by a radio frequency system. In these three fields, the field strength of the static magnetic field is high and has a large external influence. The homogeneity of the static magnetic field is also sensitive to external interference. Thus, in conventional nuclear magnetic resonance examination equipment, the use of materials containing ferrum magnetic substances is minimized or avoided. In the strong magnetic field generated by a nuclear magnetic resonance system within a certain range, when affected by the magnetic force, the ferrum magnetic substances will fly out of control to the center of the magnet, thereby creating a safety hazards for people and the equipment.

The spring-type member of a gas spring, a coil spring, etc. uses ferrum magnetic substances in the design and manufacture process to achieve the functionality of the spring (e.g., provide an elastic force). Moreover, the spring-type member may contain a large amount of ferrum magnetic substances (e.g., such as spring steel, etc.) in order to achieve good rigidity properties and a long service life. Thus, the use of the nuclear magnetic resonance imaging equipment in the prior art and the constituent parts thereof may not be taken into consideration, and the use of the spring type members may be minimized.

A spring structure in accordance with the present teachings may be used in nuclear magnetic resonance imaging equipment (e.g., superconducting nuclear magnetic resonance imaging equipment), and the influence of the magnetism of the spring structure on the homogeneity of the system static magnetic field may be reduced to an acceptable degree (e.g., such that the influence on the static field does not result in loss of imaging function). In addition, during component replacement, the spring structure is not unduly affected by the magnetic field, such that the risk of generating an uncontrollable magnetic force representing a potential safety hazards may be reduced or eliminated. In a spring structure in accordance with the present teachings, the distribution properties of the magnetic field intensity and the gradient change of the magnetic resonance system static magnetic field at the patient table are taken into consideration. As a result, the material used for the nuclear magnetic resonance imaging equipment or the patient table may include elements or features that heretofore have never been used. It is to be understood that elements and features of the various representative embodiments described below may be combined in different ways to produce new embodiments that likewise fall within the scope of the present teachings.

In some embodiments, the spring structure is a gas spring, a coil spring, or a combination thereof. By using a spring structure in accordance with the present teachings, the patient table of nuclear magnetic resonance equipment may incorporate a variety of suitable spring members. In some embodiments, the spring structure is a pressure spring structure or a pulling force spring structure.

In some embodiments, the patient table further includes a locking mechanism configured to lock the connecting rod structure at least at the high position and the low position. In some embodiments, a plurality of suitable locking mechanisms may be provided for locking the patient table at least at the high position and/or the low position. In some embodiments, the locking mechanism may also lock the patient table at a plurality of positions between the high position and the low position. In some embodiments, the locking mechanism is configured for locking at any point in a continuum. For example, a locking rod mounted to the connecting rod structure may be provided with a plurality of through-holes or elongated slots on the locking rod. The locking piece fixed with the base plane may be locked by inserting the locking piece through the through-holes. The locking piece may be locked at any position of the elongated slot.

In some embodiments, the locking mechanism includes a non-self-locking angle screw mounted to the connecting rod structure, a locking base fixed to a base plane, a pair of locking nuts sleeved on the non-self-locking angle screw, and a nut toggle mechanism mounted to the locking base. The locking base has a hole that the non-self-locking angle screw is configured to pass through in a non-threaded engagement manner (e.g., a bore hole). The nut toggle mechanism is used for toggling the pair of locking nuts to move along the axial direction of the non-self-locking angle screw. The horizontal movement of the non-self-locking angle screw may be changed to the rotation of the locking nut thereon.

In some embodiments, the nut toggle mechanism may be configured for optional toggling of the pair of locking nuts, such that the locking nuts may engage and lean against the locking base and be axially fixed with respect to the locking base (e.g., the pair of locking nuts is unable to rotate even in the absence of another rotation-limiting mechanism). In some embodiments, the locking nuts may be kept in an axial position by the nut toggle mechanism, such that the locking nuts are separated from each other and are separated from the locking base. In some embodiments, the locking mechanism may be configured to lock the vertical lift position (e.g., height) of the patient table at any point within the entire vertical lifting motion range of the patient table.

The non-self-locking angle screw may be mounted at any suitable position for realizing a desired function. In some embodiments, the non-self-locking angle screw is horizontally mounted to the flexible hinging place of the connecting rod structure (e.g., a sliding hinge). In alternative embodiments, the screw may be vertically hinged to the connecting rod.

In some embodiments, the connecting rod structure includes a first connecting rod and a second connecting rod, and the first connecting rod and the second connecting rod are arranged crosswise through a central hinge. A first end of the first connecting rod is hinged to a rack through a first fixed hinge, and a second end of the first connecting rod is slidably supported on a base plane through a first sliding hinge. A first end of the second connecting rod is hinged to the base plane through a second fixed hinge, and a second end of the second connecting rod slidably supports the rack through a second sliding hinge. Such a connecting rod structure is simple and may conveniently implement the lifting motions of the rack and the top board.

In some embodiments, a first end of the spring structure may be hinged to the first connecting rod, and a second end of the spring structure may be hinged to the second connecting rod. In some embodiments (e.g., for use in nuclear magnetic resonance imaging equipment), a horizontal configuration of the spring structure may be used. In some embodiments, the spring structure may be connected to the first connecting rod and the second connecting rod above, under, at a left side, or at a right side of the central hinge. The spring structure may be used for driving the lifting motions of the connecting rod structure and/or bearing the table. In some embodiments, the spring structure is a pressure or pulling force spring.

In some embodiments, a first end of the spring structure may be hinged to the first connecting rod part above the central hinge, and a second end of the spring structure may be hinged to the second fixed hinge. In alternative embodiments, a first end of the spring structure may be hinged to the second connecting rod part above the central hinge, and a second end of the spring structure may be hinged to the first sliding hinge.

In some embodiments, the connecting rod structure includes a first connecting rod and a second connecting rod, and the first connecting rod and the second connecting rod are arranged horizontally. A first end of the first connecting rod is hinged to a rack through a first fixed hinge, and a second end of the first connecting rod is hinged to a base plane through a second fixed hinge. A first end of the second connecting rod is hinged to the rack through a third fixed hinge, and a second end of the second connecting rod is hinged to the base plane through a fourth fixed hinge. Such a simple connecting rod structure may be used to achieve the lifting motions of the rack and the top board. Moreover, in addition to providing a lifting motion component, the connecting rod structure may also provide a horizontal rotation component.

In some embodiments, a first end of the spring structure is hinged to the first connecting rod or the second connecting rod, and a second end of the spring structure is hinged to the base plane. In some embodiments (e.g., for use in nuclear magnetic resonance imaging equipment), a horizontal configuration of the spring structure may be used.

In some embodiments, a vertical actuator or vertical motion auxiliary structure is not used, and the patient table is instead configured for manual operation by operating staff. In other embodiments, the patient table may include an auxiliary vertical actuator. Embodiments that use an auxiliary vertical actuator may use less power (e.g., only enough to fill the space or difference between the spring and the load) as compared to conventional designs.

Alternatively or additionally, the patient table may include a lever structure that may be used as a force amplification mechanism. The lever structure is hinged with the connecting rod structure through the second connecting rod structure. The lever structure may further lower the operating force exerted by operating staff.

In some embodiments, the patient table may define a rated or predetermined load value or range. In some embodiments, the spring structure (e.g., a gas spring or coil spring) is configured to have a critical position between the high position and the low position. At the critical position, the force component of the spring structure in the direction of lifting the table body is equal to the predetermined load value or a value in the predetermined load range. At the critical position, for the predetermined load value or the value in the load range, the force exerted by the operating staff (e.g., directly or with a force amplification mechanism) or the vertical actuator is zero. In the range from the low position to the critical position, the force that the spring lacks to support the load may be compensated for by the operating staff or the vertical actuator. From the critical position to the low position, a compensation force to balance the exceeded spring force and provide stable lifting may be added to the load by the operating staff or the vertical actuator. Thus, in summary, operating force may be reduced. The body weight of a patient may not correspond to the rated or predetermined weight, but rather may fall within a range. In some embodiments, the spring structure is selected such that a position where the spring bears the entire patient load may exist throughout the entire range of lifting motion of the patient table, thereby minimizing the lifting motion operating force for most people.

In some embodiments, nuclear magnetic resonance imaging equipment that includes a magnet configured to generate a static magnetic field and a patient table in accordance with the present teachings are provided. An included angle between the orientation of the spring structure and an orientation of a nearby static magnetic field is less than or equal to $\pm 15°$, in some embodiments less than or equal to $\pm 10°$, and in some embodiments less than or equal to $\pm 5°$. In some embodiments, the orientation of the spring structure is parallel to the direction of the static magnetic field.

The influence of the magnetism of the spring structure on the homogeneity of the system static magnetic field of the nuclear magnetic resonance imaging equipment may be reduced to an acceptable extent (e.g., such that imaging function is not lost). During replacement of components, the spring structure may not be unduly affected by the magnetic field, thereby lowering or eliminating the risk of generating an uncontrollable magnetic force and potential safety hazards).

In some embodiments (e.g., for use in nuclear magnetic resonance imaging equipment), the spring structure is arranged horizontally. As a result of the horizontal extension orientation of the spring structure, the influence of the magnetism of the spring structure on the homogeneity of the system static magnetic field may be reduced to an acceptable degree (e.g., such that the influence on the static field is not sufficient to result in the loss of imaging function). In addition, during replacement of components, the spring structure may not be extensively affected by the magnetic field, thereby reducing or eliminating the risk of generating an uncontrollable magnetic force and potential safety hazards. Moreover, a conventional magnet configuration may be selected for the nuclear magnetic resonance components.

Other characteristics and advantages of the present teachings will be given in conjunction with exemplary embodiments and implementations hereinafter.

BRIEF DESCRIPTION OF THE DRAWINGS

In the drawings, the same or similar features are represented by the same or similar reference characters.

DETAILED DESCRIPTION

Figure 1:
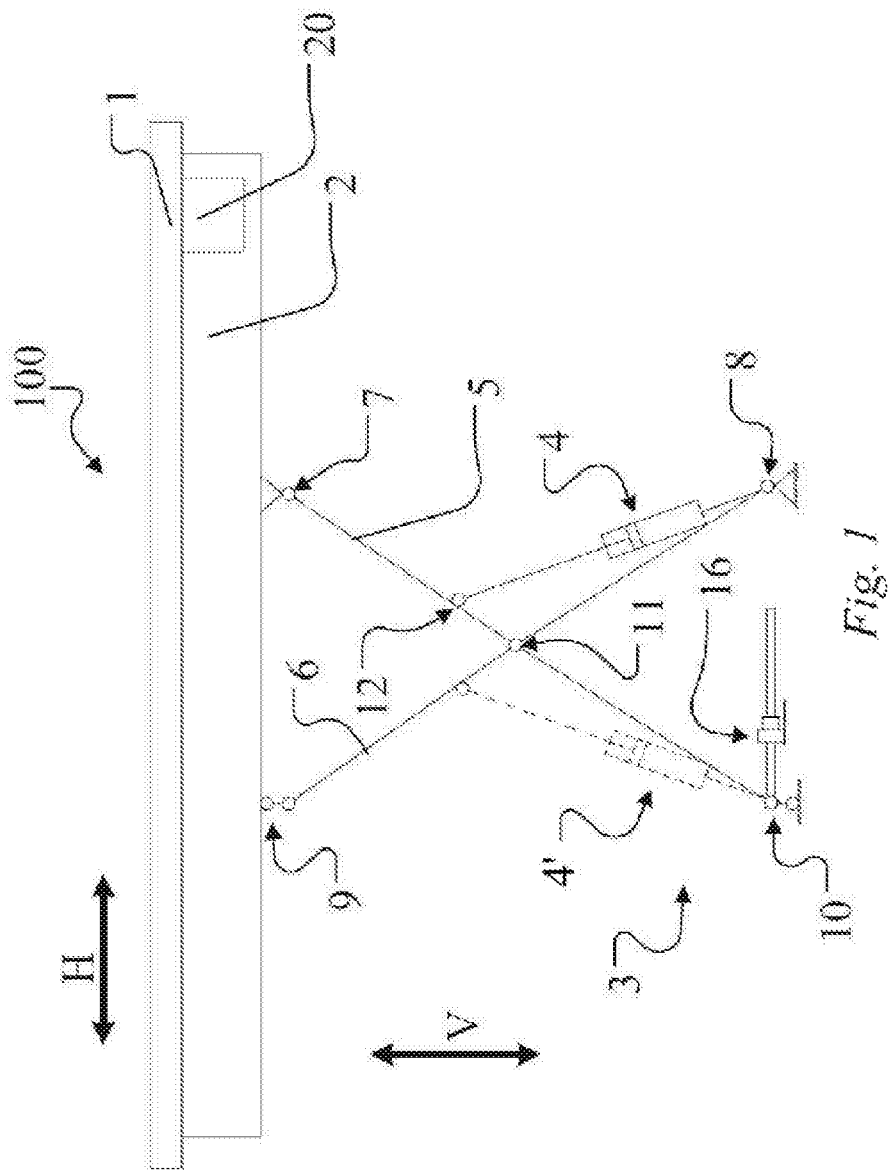
FIG. 1 is a schematic diagram of an exemplary first patient table (PTAB) shown at a lifted first position.

Exemplary embodiments will now be described with reference to the accompanying drawings. Although the accompanying drawings are provided to illustrate exemplary implementations in accordance with the present teachings, the accompanying drawings may not reflect the actual size or shape of particular embodiments. In addition, for the sake of clarity, some features may be magnified, removed, partially sectioned or shown in schematic form. As used herein, the phrase "in the accompanying drawings" and similar expressions may not refer simultaneously to all of the accompanying drawings or examples.

As used herein, the directional terms used to describe the accompanying drawings (e.g., "above," "under," "left," "right," "upward," "downward," and the like) have their normal meanings. Unless otherwise indicated, the directional terms are intended to represent corresponding directions vis-à-vis the patient table and corresponding imaging equipment.

As used herein the terms "approximately" or "substantially" are intended to include approximate states of features described by that term (e.g., that are equivalent in an engineering sense). As used in reference to a number or a number range, the term "approximately" is intended to include fluctuations based on the number or number range.

As used herein, the term "connecting rod" or "connecting rod structure" is intended to include connecting rods of a type known in the art, and any structure or mechanism containing such a connecting rod.

As used herein, the terms "high position" and "low position" refer, respectively, to an upper limit (e.g., the highest height) and a lower limit (e.g., the lowest height) in the vertical lifting motion range of a patient table. These terms are used for indicating the limit values of the vertical lift range for a product configuration, and do not imply that the patient table has a theoretical upper limit or lower limit. A plurality of different suitable lifting ranges for different patient tables, and "high positions" and "low positions" thereof, may be selected in accordance with the present teachings. For example, in some embodiments, the position where the patient table is lifted for horizontally transferring the top board to the imaging equipment may serve as the "high position." In other embodiments, the "low position" may refer to the position where the patient table is lowered to allow a patient to conveniently mount onto the table, the position where the patient table is lowered for maintenance and examination, or a position that is even lower than one or both of these two positions.

As used herein, the term "load" or "bearing" refers to the weight of a load-bearing feature per se and the weights of other objects born on that feature. For example, the "loads" of the rack and the top board include the weights of the rack and the top board per se and the weight of the patient (if present) lying down thereon. As used herein, the phrase "patient table load" may also be used and the weights of the connecting rods and the spring component per se may be substantially neglected.

As used herein, the term "base plane" refers to a part that may be regarded as being immobilized in the coordinate system of the patient table. The "base plane" includes but is not limited to the ground, the immobilized base, or the like. By way of example, if feature A and feature B are mounted or supported on the base plane, feature A and feature B may be mounted or supported on different immobilized parts.

As used herein, the terms "first" and "second" are used solely for convenience to distinguish between two similar structures or features. Unless otherwise indicated, the terms "first" and "second" are not intended to convey a priority or specific orientation and may be used interchangeably. The positions or configurations of corresponding structures or features may be determined by the defined or described relationships with other components or features. For example, a fixed hinge provided on a base plane may be referred to as the first fixed hinge, and a fixed hinge provided at the bottom of a rack may be referred to as the second fixed hinge, without changing the substances of these respective features.

Figure 2:
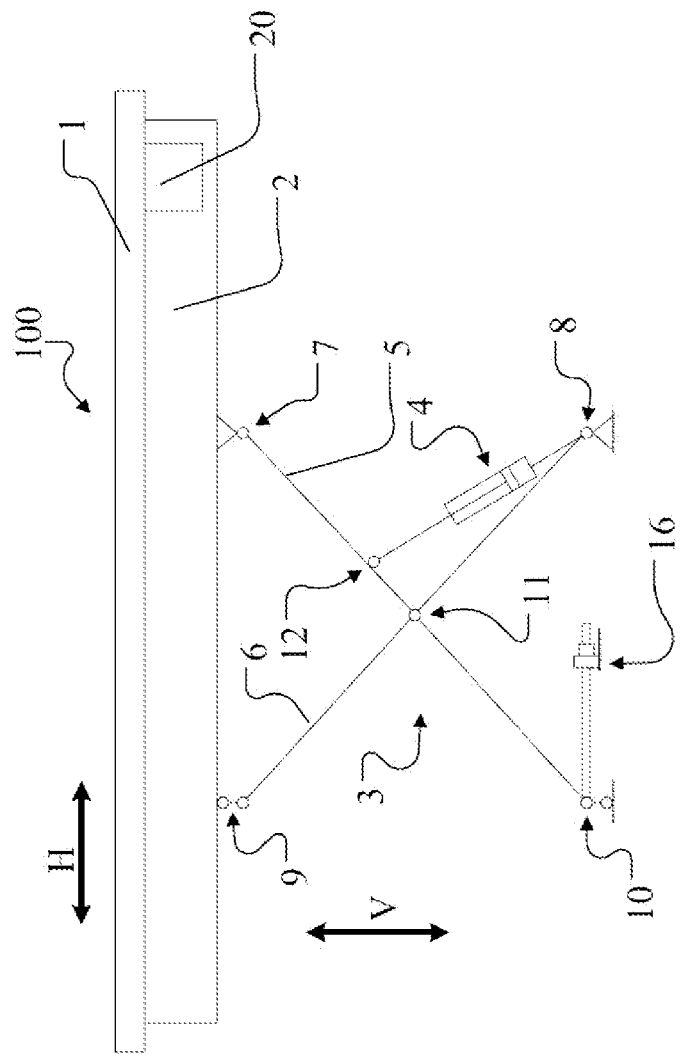
FIG. 2 is a schematic diagram of the exemplary patient table of FIG. 1 shown at a lowered second position.

FIGS. 1 and 2 show an exemplary first embodiment of a patient table 100 that may be used in various imaging equipment. The patient table 100 may include a table body, a (first) connecting rod structure 3 arranged on a base plane (e.g., the ground or a fixed base) and configured for supporting the table body, and a spring structure in the form of a pressed gas spring 4. The gas spring 4 may be made of spring steel or contain a pressed coil spring replacement of a spring or a spring structure.

As shown in FIGS. 1 and 2, the table body may include a top board 1 configured for bearing a patient, and a rack 2 under the top board 1 configured for supporting the top board 1. In addition, the patient table 100 may also include a horizontal actuator 20. At the lifted first position of the patient table shown in FIG. 1 (e.g., the high position), the horizontal actuator 20 drives the top board 1 to perform a horizontal motion H on the rack. As a result, a patient thereon may be carried into or be returned from the target examination position inside the imaging equipment. The horizontal actuator may include any type of suitable actuator.

The connecting rod structure 3 provided under the rack 2 supports the rack 2 and the top board 1 and may be operated to enable the rack 2 and the top board to perform a vertical (e.g., lifting) motion V. For example, by directly or indirectly operating the connecting rod structure, the rack 2 and the top board 1 may perform a lifting motion between the lifted first position shown in FIG. 1 (e.g., the high position) and the lowered second position shown in FIG. 2 (e.g., the low position). The patient table 100 also provides a locking mechanism 16 configured for locking the connecting rod structure 3 at least at the high position and the low position, so as to lock the patient table at a corresponding vertical position. In some embodiments, the locking mechanism 16 may provide locking within the entire lifting range of the patient table 100. An exemplary embodiment of the locking mechanism will be further described below in reference to FIG. 7.

As shown in FIGS. 1 and 2, one embodiment of the connecting rod structure 3 has a "scissor-shaped" configuration, and may include a first connecting rod 5 and a second connecting rod 6 arranged crosswise. A central hinge 11 is provided at the intersection of the first connecting rod 5 and the second connecting rod 6. The first connecting rod 5 and the second connecting rod 6 of the "scissor-shaped" connecting rod structure 3 may fold or unfold at the central hinge 11. The first end of the first connecting rod 5 may be hinged to the bottom side of the rack 2 through a first fixed hinge 7, and the second end of the first connecting rod 5 may be slidably supported on the base plane through the first sliding hinge 10. The first end of the second connecting rod 6 may be hinged to the base plane through a second fixed hinge 8, and the second end of the second connecting rod 6 may be slidably supported on the bottom side of the rack 2 through the second sliding hinge 9. Hence, by directly or indirectly operating the connecting rod structure 3 (e.g., the unlocked state of the locking mechanism), the rack 2 and the top board 1 may be lifted or lowered. When the rack 2 and the top board 1 are being lifted, the first sliding hinge 9 and the second sliding hinge 10 approach, respectively, the first fixed hinge 7 and the second fixed hinge 8 along the bottom side of the rack 2 and the base plane. When the rack 2 and the top board 1 are being lowered, the first sliding hinge 9 and the second sliding hinge 10 slide away, respectively, from the first fixed hinge 7 and the second fixed hinge 8 along the bottom side of the rack 2 and the base plane. In the exemplary embodiment shown in FIG. 1, the first connecting rod 5 and the second connecting rod 6 have substantially the same length and are mirror symmetric with each other about a vertical line through the central hinge 11. In other embodiments, the first connecting rod 5 and the second connecting rod 6 do not have the same length and/or are asymmetric.

A first end of the gas spring 4 may be hinged to the first connecting rod 5 above the central hinge 11, and a second end of the gas spring 4 may be hinged to the second fixed hinge 8. In other embodiments, a first end of the gas spring 4' (shown in dashed lines as an alternative) may be hinged to one side of the second connecting rod 6 (e.g., above the central hinge 11), and a second end of the gas spring 4 may be correspondingly hinged to the second sliding hinge 10.

Figure 3:
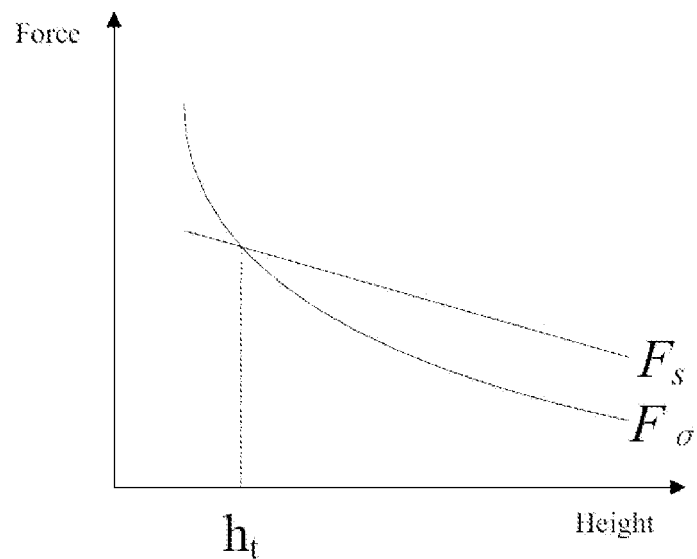
FIG. 3 is a graph of the force and height in the exemplary patient table of FIGS. 1 and 2.
Figure 4:
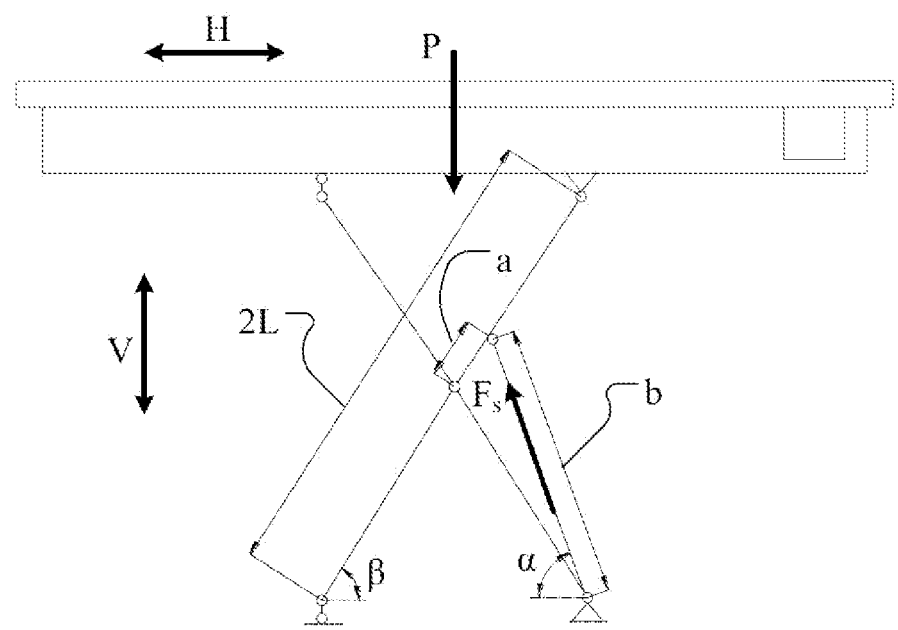
FIG. 4 is a schematic diagram of the exemplary patient table of FIG. 1 shown under force.

FIG. 4 shows a schematic diagram of the patient table in FIG. 1 under force. In FIG. 4, for the sake of clarity, the gas spring is shown in simplified form as a straight line. As shown in FIG. 4, the lengths of the first connecting rod and the second connecting rod may be 2L, the length of the gas spring 4 may be b, and the length between the hinged part 12 of the gas spring connected with the connecting rod and the central hinge 11 may be a. The included angle between the first connecting rod 5 and the horizontal direction is α, and the included angle between the gas spring and the horizontal direction is β. The elastic force exerted by the gas spring is $F_s$, and the bearing is P (e.g., the weights of the rack and the top board per se and the weight of the patient if present). As shown in FIG. 3, the force vector component resolved from the bearing P to the direction where the gas spring extends is represented by $F_\sigma$. During lifting, the above-described gas spring length b is a variable that varies with the lifted height, and the angles α and β also vary accordingly (cf. FIGS. 1 and 2). According to the theory of machines and mechanisms, the relationship between the force vector $F_\sigma$ and the load P is as follows:

$$F_\sigma = \frac{P \cdot b}{a \cdot \sin\beta}$$

For the elastic force of the gas spring 4 (or other spring structures), $F_s$=kb, where k is the elasticity coefficient.

As shown in FIG. 3, a suitable gas spring may be selected such that a transition height $h_t$ (e.g., critical position) may exist between the high position and the low position of the patient table. The elastic force $F_s$ is equal to the force vector $F_\sigma$ of the load P in the direction that the spring extends. At this position (e.g., height), the component of the elastic force of the gas spring is equal to the load in the lifting motion direction. With such an arrangement, as shown in FIG. 3, the force to be exerted at this position by operating staff (e.g., either directly or with a force amplification mechanism) or by the vertical actuator is zero. Between the first position and the transition position, the spring is still not sufficient to support the load. Thus, the operating staff and the actuator may provide a vertically upward force component, such that the rack, the top board, and the like may rise in this range. Between the preceding transition height $h_t$ (e.g., the critical position) and the second position, the spring force will exceed the load P (e.g., the force vector component $F_\sigma$), and the operating staff and the actuator may provide a vertically downward compensation force component. The operating force for lifting of the patient table 100 may be reduced.

A rated or predetermined load value or range may be selected by sampling, selecting experience data, or the like, such that the above-described transition height $h_t$ (e.g., the critical position) may exist for the rated or predetermined load value or range during the lifting of the patient table 100, thereby providing a reduced operating force. In alternative embodiments, suitable springs may be selected according to other criteria based on the concept of transition height $h_t$ (e.g., the critical position), such that the operating force for vertically lifting the patient table may be optimized (e.g. minimized).

Figure 5:
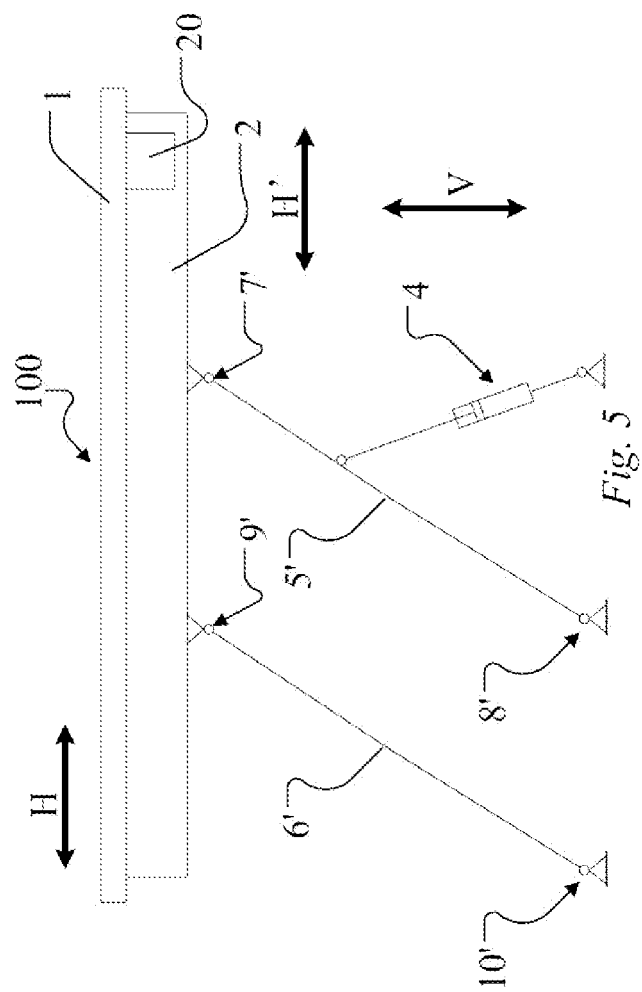
FIG. 5 is a schematic diagram of an exemplary second patient table.

FIG. 5 shows a second exemplary embodiment that differs from the above-described first exemplary embodiment in that the connecting rod 3 includes a first connecting rod 5' and a second connecting rod 6' that are arranged in parallel. The first connecting rod 5' and the second connecting rod 6' are hinged, respectively, onto the bottom side of the rack 2 and the base plane through the first fixed hinge 7' and the second fixed hinge 8', and the third fixed hinge 9' and the fourth fixed hinge 10'. In addition, a first end of the gas spring 4 is hinged to the first connecting rod 5', and a second end of the gas spring 4 is hinged to the base plane. The vertical lifting component V of the rack 2 and the top board 1 may be provided by the wiggle of the first connecting rod 5' and the second connecting rod 6', and the horizontal motion component H' may be generated at the same time.

Figure 6:
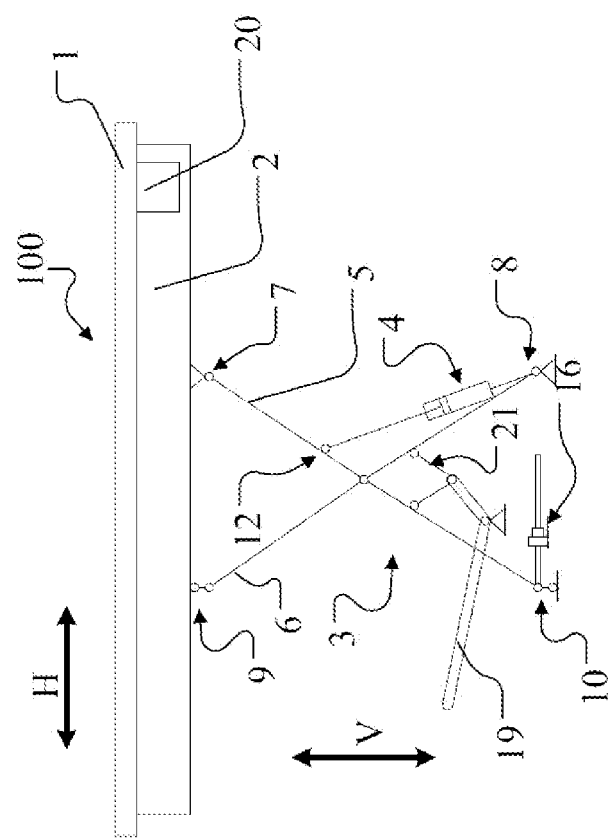
FIG. 6 is a schematic diagram of an exemplary third patient table.

FIG. 6 shows an exemplary third embodiment that is substantially similar to the exemplary first embodiment shown in FIG. 1. A force amplification mechanism for manual operation is included to facilitate operation by the operating staff. As shown in FIG. 6, a lever structure 19 is provided. A pivot of the lever structure is fixedly hinged with a base plane. A first end of the lever structure is operatively connected to the first connecting rod and the second connecting rod under a central hinge 11 through a second connecting rod structure 21. A second free end of the lever structure is operable by the operating staff. Although FIG. 6 shows the lever structure being provided on the opposite side of the gas spring, the lever structure may alternatively be provided on the same side as the gas spring. In other embodiments, the lever structure and corresponding components may be provided by other mechanisms configured for amplifying the operating force.

Alternatively or additionally, a vertical actuator (e.g., an electric motor) of a conventional type may be used (e.g., at low power).

Figure 7:
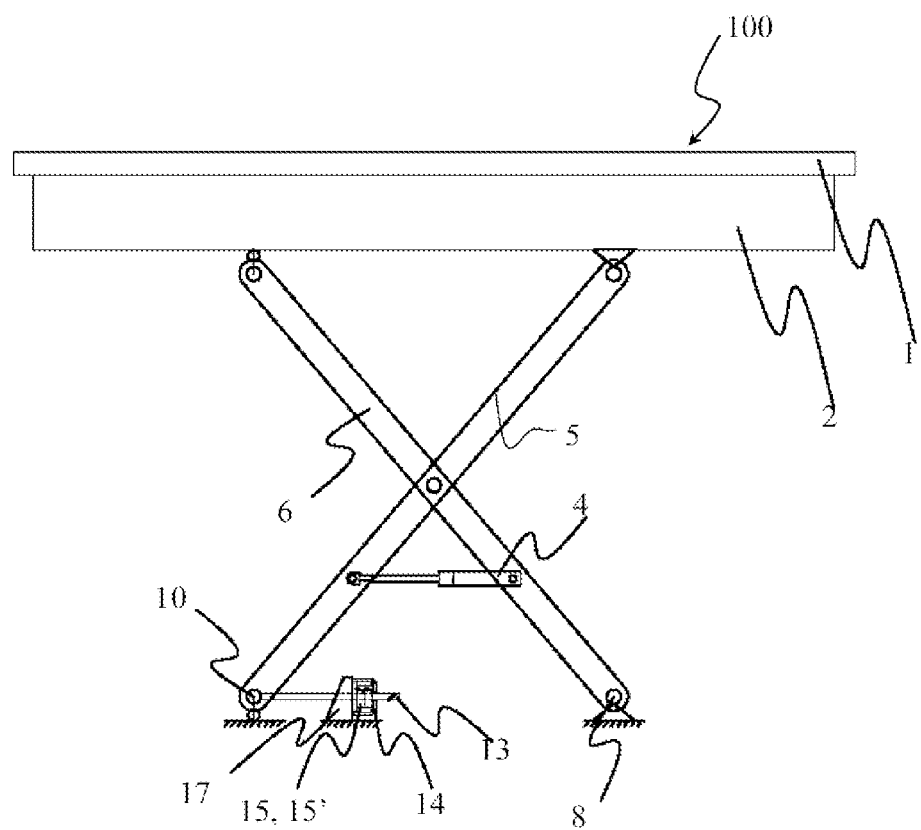
FIG. 7 is a schematic diagram of an exemplary fourth patient table configured for use in MRI equipment.

FIG. 7 shows an exemplary fourth embodiment for use in nuclear magnetic resonance equipment (e.g., superconducting magnetic resonance equipment). Members or materials that may provide advantages but that have been heretofore avoided in conventional designs may be used without diminishing the performance of the magnetic resonance equipment. Apart from the gas spring (e.g., or other suitable spring structures), the components and configuration of the exemplary fourth embodiment shown in FIG. 7 are substantially similar to the exemplary first embodiment shown in FIG. 1. As shown in FIG. 7, the gas spring 4 is horizontally oriented. A first end of the gas spring 4 is hinged to a first connecting rod 5 under the central hinge 11, and a second end of the gas spring 4 is hinged to the second connecting rod 6 part under the central hinge 11. To support the loads of the rack and the top board, the gas spring 4 may be in the form of a pulling gas spring. The exemplary embodiment shown in FIG. 7 may provide a patient examination platform configured for using reduced operating force that does not result in a concomitant reduction in imaging effect. The gas spring is provided in an orientation parallel to the direction of the static magnetic field (e.g., at the position of the gas spring) generated by the magnetic resonance equipment (e.g., superconducting MRI equipment). Such a spring configuration may also avoid or substantially reduce the risks caused by generating magnetization.

Arranging the spring parallel to the magnetic field in accordance with the present teachings may likewise be implemented in connection with other embodiments described herein in order to obtain new embodiments that likewise fall within the scope of the present teachings. For example, the horizontally arranged spring may be combined with the above-described second embodiment. A first end of the horizontally arranged spring may be hinged to the first connecting rod 5' or the second connecting rod 6', and a second end of the horizontally arranged spring may be hinged to the base plane (e.g., the fixed part). The spring may be a pressed spring (e.g., mounted from a first side to the connecting rod) or a pulling spring (e.g., mounted from a second side to the connecting rod). In configurations where the spring is arranged parallel to the magnetic field in accordance with the present teachings, a variety of materials and configurations may be used for the spring.

Although the orientation at the patient table of the static magnetic field of common magnetic resonance equipment (e.g., the position where the spring may be provided) is horizontal, other orientations of the static magnetic field may also be used. If the static magnetic field where the spring is mounted is in a different orientation, the spring may be correspondingly arranged according to an orientation parallel to the static magnetic field.

FIG. 7 shows a locking mechanism 16. Although a plurality of locking mechanisms may be provided, for example, the locking mechanisms may lock the rack and the top board only at the lifted first position and the lowered second position. The locking mechanism 16 may lock the patient table at any position (e.g., height) in the lifting range. The locking mechanism 16 includes a screw 13, a locking base 17 fixed to the base plane, a pair of locking nuts 15 and 15', and a nut toggle mechanism 14. One end of the screw 13 is mounted to the second sliding hinge 10. The screw 13 passes through the bore hole in the locking base 17. The pair of locking nuts 15 and 15' is sleeved on the other side of the screw 13. The nut toggle mechanism 14 is rotatably mounted to the locking base 17. To lock the patient table, the nut toggle mechanism 14 may be rotated in one direction. The nut toggle mechanism 14 may be screwed onto the screw 13 for axial movement, such that the pair of locking nuts 15 and 15' may engage with each other and lean against the position of the locking base 17. The pair of locking nuts 15 and 15' may be axially fixed with respect to the locking base 17 by the nut toggle mechanism. Since the thread pitches of the two locking nuts may differ slightly (e.g., tolerance difference), the threads of the pair of nuts cannot rotate with respect to the thread of the screw even without other structures to restrict rotation of the nuts with respect to the screw. Thus, a locking position limit for the connecting rod structure 3 is provided. However, when a lifting operation is desired, the nut toggle mechanism may be operated to rotate in an opposite direction, such that the two nuts are separated from each other and also separated from the locking base 17. The pair of nuts may rotate with respect to the screw, and the screw may be allowed to move horizontally by engaging with the threads of the nuts. The sliding hinge is allowed to move along the axial direction, thereby allowing lifting of the patient table.

In some embodiments, the locking mechanism 16 may be used at a suitable position of another sliding hinge, a first connecting rod, or a second connecting rod. In addition, other types of suitable locking mechanisms including conventional locking mechanisms may also be used in accordance with the present teachings.

Some embodiments of a patient table in accordance with the present teachings may be applicable to magnetic resonance (MRI) equipment. In some embodiments, magnetic resonance equipment or assemblies equipped with a patient table as described herein are provided.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A patient table for nuclear magnetic resonance imaging equipment, the patient table comprising:
   a table body configured for bearing a patient;
   a connecting rod structure configured for supporting the table body, wherein the connecting rod structure is operable to move the table body between a high position and a low position; and
   a spring structure having a first fixed end and a second fixed end, wherein at least one end of the first fixed end and the second fixed end is hinged to the connecting rod structure, and wherein the spring structure is configured for driving movement of the connecting rod structure, bearing the table body, or driving movement of the connecting rod structure and bearing the table body using elastic force, wherein an angle between an orientation of the spring structure and a horizontal direction is less than or equal to ±15° from the horizontal direction for at least the high position, wherein the connecting rod structure comprises a first connecting rod and a second connecting rod, and wherein the first connecting rod and the second connecting rod are arranged crosswise through a central hinge, wherein a first end of the first connecting rod is hinged to a rack through a first fixed hinge, and wherein a second end of the first connecting rod is slidably supported on a base plane through a first sliding hinge, wherein a first end of the second connecting rod is hinged to the base plane through a second fixed hinge, and wherein a second end of the second connecting rod slidably supports the rack through the second sliding hinge, and wherein a first end of the spring structure is hinged to the first connecting rod above the central hinge, and a second end of the spring structure is hinged to the second fixed hinge, or wherein a first end of the spring structure is hinged to the second connecting rod above the central hinge and a second end of the spring structure is hinged to the first sliding hinge.

2. The patient table of claim 1, wherein the angle between the orientation of the spring structure and the horizontal direction is less than or equal to ±10° from the horizontal direction for at least the high position.

3. The patient table of claim 2, wherein the spring structure comprises a gas spring, a coil spring, or a combination thereof.

4. The patient table of claim 1, wherein the spring structure is oriented horizontally.

5. The patient table of claim 4, wherein the spring structure comprises a gas spring, a coil spring, or a combination thereof.

6. The patient table of claim 1, wherein the spring structure comprises a gas spring, a coil spring, or a combination thereof.

7. The patient table of claim 1, wherein a first end of the spring structure is hinged to the first connecting rod, and wherein a second end of the spring structure is hinged to the second connecting rod.

8. The patient table of claim 1, further comprising:
an auxiliary vertical actuator;
or a lever structure, wherein the lever structure is hinged with the connecting rod structure through a second connecting rod structure.

9. The patient table of claim 1, wherein the patient table comprises a predetermined load value or a predetermined load range;
wherein the spring structure is configured to have a critical position between the high position and the low position; and
wherein, at the critical position, a force component of the spring structure in a lifting direction of the table body equals the predetermined load value or a value in the predetermined load range.

10. A nuclear magnetic resonance imaging apparatus comprising:
a magnet configured to generate a static magnetic field; and
a patient table comprising:
a table body configured for bearing a patient;
a connecting rod structure configured for supporting the table body, wherein the connecting rod structure is operable to move the table body between a high position and a low position;
a spring structure having a first fixed end and a second fixed end, wherein at least one end of the first fixed end and the second fixed end is hinged to the connecting rod structure, and wherein the spring structure is configured for driving movement of the connecting rod structure, bearing the table body, or driving movement of the connecting rod structure and bearing the table body with an elastic force; and
a locking mechanism configured to lock the connecting rod structure at least at the high position and the low position, wherein the locking mechanism comprises:
a non-self-locking angle screw mounted to the connecting rod structure;
a locking base fixed to a base plane;
a pair of locking nuts sleeved on the non-self-locking angle screw; and
a nut toggle mechanism mounted to the locking base;
wherein an angle between an orientation of the spring structure and an orientation of a nearby static magnetic field is less than or equal to ±15° from the orientation of the nearby static magnetic field,
wherein the locking base comprises a hole, the non-self-locking angle screw configured to pass through the hole in a non-threaded engagement manner; and
wherein the nut toggle mechanism is configured for toggling the pair of locking nuts to move along an axial direction of the non-self-locking angle screw.

11. The nuclear magnetic resonance imaging apparatus of claim 10, wherein the orientation of the spring structure is parallel to the orientation of the nearby static magnetic field.

12. A patient table comprising:
a table body configured for bearing a patient;
a connecting rod structure configured for supporting the table body, wherein the connecting rod structure is operable to move the table body between a high position and a low position;
a spring structure having a first fixed end and a second fixed end, wherein at least one end of the first fixed end and the second fixed end is hinged to the connecting rod structure, and wherein the spring structure is configured for driving movement of the connecting rod structure, bearing the table body, or driving movement of the connecting rod structure and bearing the table body; and
a locking mechanism configured to lock the connecting rod structure at least at the high position and the low position, the locking mechanism comprising:
a non-self-locking angle screw mounted to the connecting rod structure;
a locking base fixed to a base plane;
a pair of locking nuts sleeved on the non-self-locking angle screw; and
a nut toggle mechanism mounted to the locking base;
wherein the locking base comprises a hole, the non-self-locking angle screw configured to pass through the hole in a non-threaded engagement manner; and
wherein the nut toggle mechanism is configured for toggling the pair of locking nuts to move along an axial direction of the non-self-locking angle screw.

13. The patient table of claim 12, wherein the connecting rod structure comprises a first connecting rod and a second connecting rod arranged in parallel;
wherein a first end of the first connecting rod is hinged to a rack through a first fixed hinge, and wherein a second end of the first connecting rod is hinged to a base plane through a second fixed hinge; and wherein a first end of the second connecting rod is hinged to the rack through a third fixed hinge, and a second end of the second connecting rod is hinged to the base plane through a fourth fixed hinge.

14. The patient table of claim 13, wherein a first end of the spring structure is hinged to the first connecting rod or the second connecting rod, and wherein a second end of the spring structure is hinged to the base plane.

* * * * *